United States Patent
Horioka et al.

(10) Patent No.: US 9,517,282 B2
(45) Date of Patent: Dec. 13, 2016

(54) LIGHT IRRADIATION APPARATUS

(71) Applicant: Nikkiso Co., Ltd., Tokyo (JP)

(72) Inventors: Satoru Horioka, Tokyo (JP); Masato Fujiwara, Tokyo (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 14/732,500

(22) Filed: Jun. 5, 2015

(65) Prior Publication Data

US 2015/0265734 A1    Sep. 24, 2015

Related U.S. Application Data

(63) Continuation of application No. PCT/JP2013/006972, filed on Nov. 27, 2013.

(30) Foreign Application Priority Data

Dec. 6, 2012    (JP) .................................. 2012-267632

(51) Int. Cl.
  A61L 2/10    (2006.01)
  A61N 5/06    (2006.01)
  H01L 33/54    (2010.01)

(52) U.S. Cl.
  CPC ............... *A61L 2/10* (2013.01); *A61N 5/0624* (2013.01); *H01L 33/54* (2013.01)

(58) Field of Classification Search
  USPC .......................... 250/453.11, 454.11, 455.11, 493.1,250/504 R; 422/22, 24
  See application file for complete search history.

(56) References Cited

U.S. PATENT DOCUMENTS

2006/0131246 A1*  6/2006  Ehlers, Sr. .................... 210/748
2006/0271024 A1   11/2006 Gertner et al.
2013/0274549 A1* 10/2013  Natale .................. A61N 5/0624
                                                              600/104

FOREIGN PATENT DOCUMENTS

| CN | 102784434 A | 11/2012 |
|---|---|---|
| JP | 07-275200 | 10/1995 |
| JP | 10-190058 | 7/1998 |
| JP | 10-216085 | 8/1998 |
| JP | 2005-013723 | 1/2005 |
| JP | 2007-000618 | 1/2007 |
| JP | 2008-528188 A | 7/2008 |
| WO | WO 2006/081312 A2 | 8/2006 |

OTHER PUBLICATIONS

Supplementary European Search Report and Opinion issued in corresponding EP Application No. 13859864.4, issued on Aug. 9, 2016.

* cited by examiner

*Primary Examiner* — Nicole Ippolito

(74) *Attorney, Agent, or Firm* — Muncy, Geissler, Olds & Lowe, P.C.

(57) ABSTRACT

In a light irradiation apparatus, an elongated body has flexibility that allows for elastic restoration. An LED chip is closely fixed to a tip portion of the elongated body and emits ultraviolet light. A cover unit covers the LED chip so as to protect the LED chip and allows the ultraviolet light emitted by the LED chip to pass through the cover unit. A conductive unit extends in a longitudinal direction of the elongated body and passes electric current for allowing the LED chip to emit light. An insulation unit covers the conductive unit so as to ensure electrical insulation of the conductive unit.

12 Claims, 4 Drawing Sheets

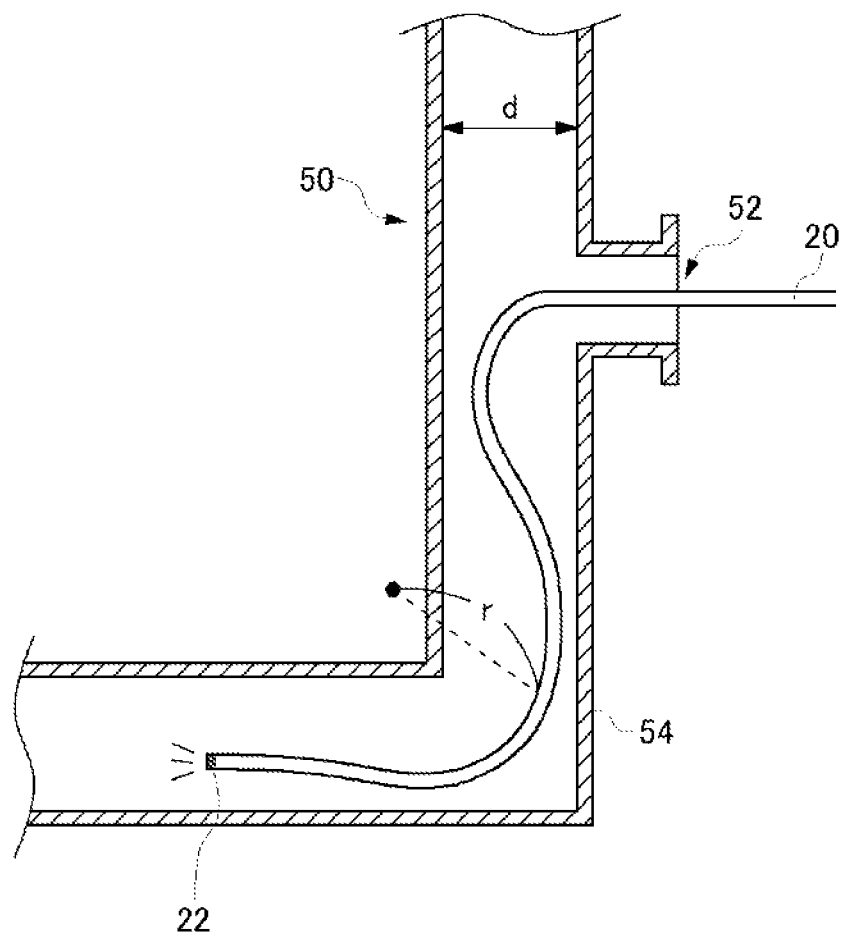

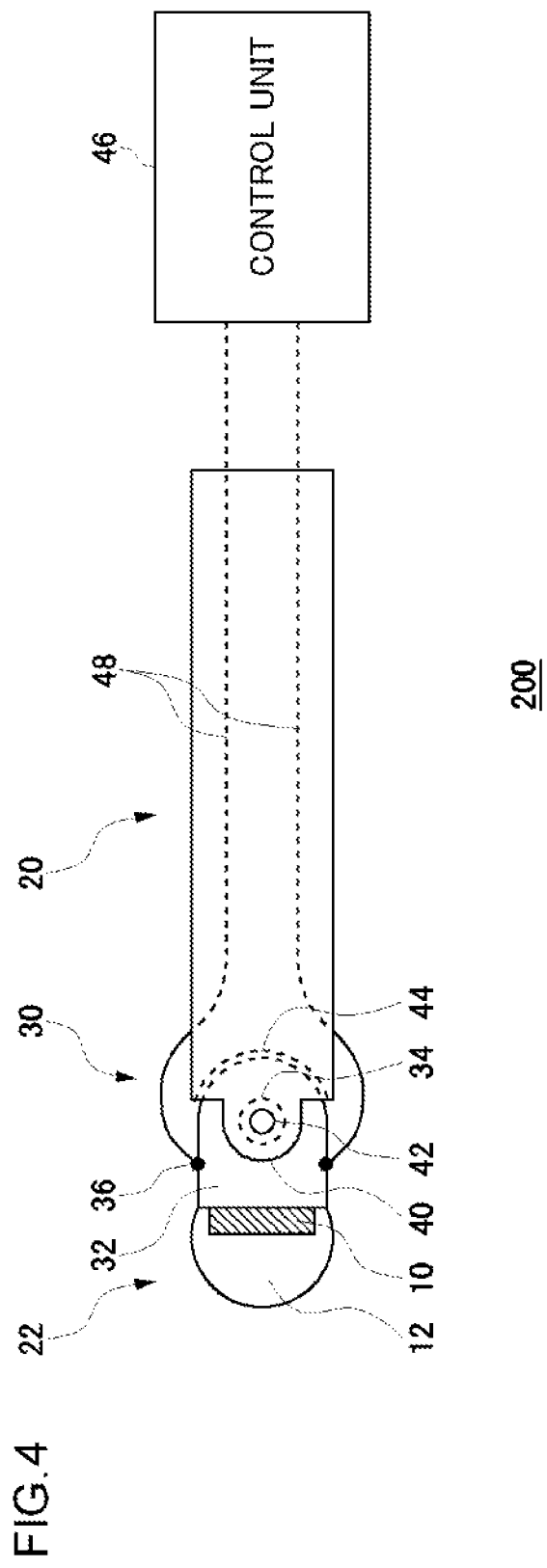

LIGHT IRRADIATION APPARATUS

RELATED APPLICATION

Priority is claimed to Japanese Patent Application No. 2012-267632, filed on Dec. 6, 2012, the entire content of which is incorporated herein by reference.

BACKGROUND

1. Field of the Invention

The present invention relates to a light irradiation apparatus and particularly to an apparatus that irradiates a narrow part with light.

2. Description of the Related Art

Ultraviolet light is widely used in the field of resin curing by ultraviolet light, or in the field of medical treatment and food for sterilization, disinfection treatment, or the like. Recently, with an increase in people's interest in food safety and sanitation, prevention of infection with bacteria including O-157, influenza viruses, and the like is considered important, and there is a need for apparatuses that are capable of effectively performing disinfection treatment.

In factories where food or medical and pharmaceutical products are manufactured, manufacturing equipment is often disassembled and cleaned on a regular basis in order to maintain hygiene so as to remove dirt inside the equipment, and disinfection treatment is often performed by irradiation with ultraviolet light. For example, there are apparatuses that perform disinfection by radiating ultraviolet light through optical fibers that are inserted in pipes so that disinfection inside the pipes can be performed by irradiation with ultraviolet light in manufacturing equipment in which narrow pipes and/or bent pipes are used.

However, optical fibers allow for the entry of only light that is in a predetermined range of incident angles determined by the numerical aperture thereof, and, in general, only a portion of light emitted by a light source can be introduced into the fibers. In particular, when optical fibers having a small core diameter are used in order to irradiate a narrow part with light, the introduction efficiency of the light becomes lowered, and only around several percent of light from a light source can be guided depending on a core diameter that is selected.

SUMMARY OF THE INVENTION

In this background, a purpose of the present invention is to provide a light irradiation apparatus capable of effectively irradiating even a narrow part with light.

A light irradiation apparatus according to one embodiment of the present invention includes: an elongated body; and a light emitting diode (LED) chip that is closely fixed to a tip portion of the elongated body. The elongated body has: a conductive unit that extends in a longitudinal direction of the elongated body and that passes electric current for allowing the LED chip to emit light; and an insulation unit that covers the conductive unit so as to ensure electrical insulation of the conductive unit.

According to the light irradiation apparatus of the above embodiment, a narrow part inside a pipe or the like can be irradiated with light by inserting the elongated body to which the LED chip is fixed at the tip portion and passing electric current through the conductive unit in that state so as to allow ultraviolet light to be emitted from the LED chip. Also, since almost all the light emitted by the LED chip can be radiated to the inside of the pipe, light emitted by the LED chip, which is a light source, can be efficiently utilized compared to a case where optical fibers are used.

In the light irradiation apparatus of the above embodiment, the LED chip may emit ultraviolet light.

The light irradiation apparatus of the above embodiment may further include a cover unit that covers the LED chip so as to protect the LED chip and that allows the ultraviolet light emitted by the LED chip to pass therethrough.

In the light irradiation apparatus of the above embodiment, the elongated body may have flexibility that allows for elastic restoration.

The light irradiation apparatus of the above embodiment may further include: a bending mechanism that is provided near the tip portion and that allows a vicinity of the tip portion to be bent; and a control unit that allows a bending direction by the bending mechanism to be controlled from an end portion on the side opposite to the tip portion in the elongated body.

Optional combinations of the aforementioned constituting elements, and implementations of the present invention in the form of methods, apparatuses, or systems may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 3 is a diagram illustrating an elongated body inserted into a bent pipe; and FIG. 4 is a diagram illustrating a light irradiation apparatus according to an exemplary variation.

DETAILED DESCRIPTION OF THE INVENTION

Described below is an explanation of the embodiments of the present invention with reference to figures. In the figures, like numerals represent like constituting elements, and the description thereof is omitted appropriately.

Figure 1:
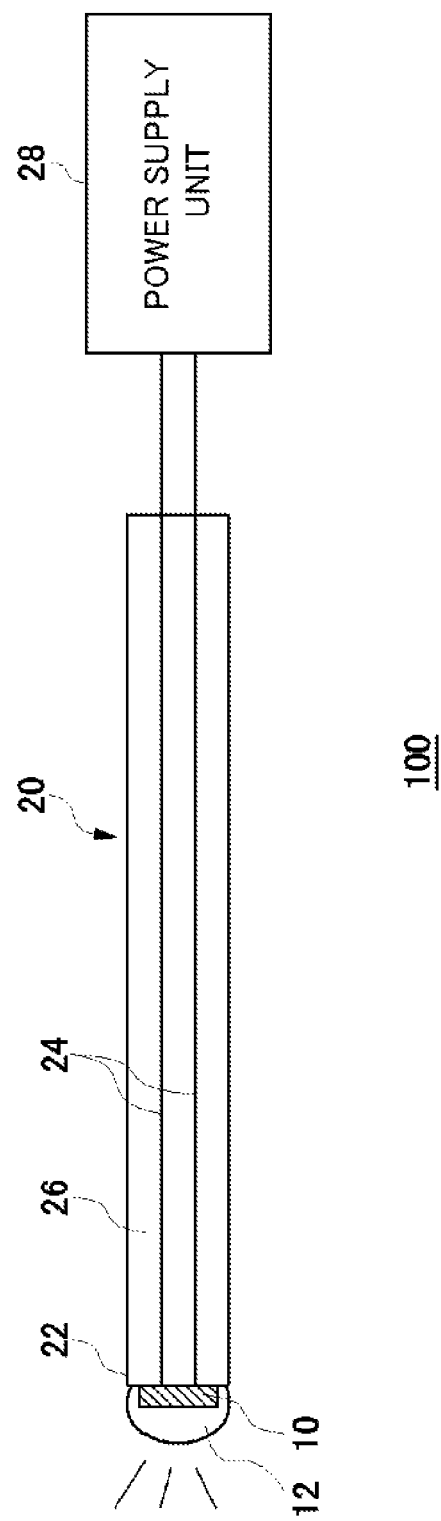
FIG. 1 is a diagram illustrating a light irradiation apparatus according to an embodiment.
Figure 2:
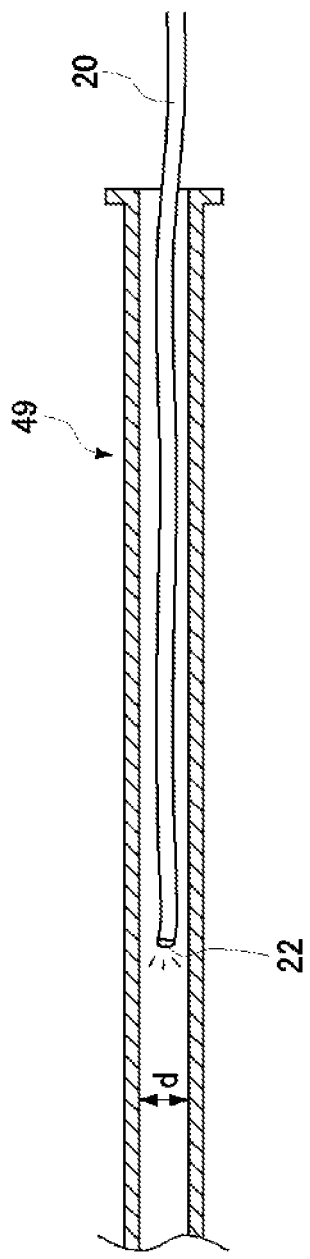
FIG. 2 is a diagram illustrating an elongated body inserted into a narrow pipe with a small inner diameter.

FIG. 1 illustrates a light irradiation apparatus 100 according to an embodiment. The light irradiation apparatus 100 performs disinfection treatment by irradiating, while an elongated body 20 is inserted in a narrow pipe with a small inner diameter, a bent pipe, or the like as shown in FIGS. 2 and 3, the inside of the pipe and a narrow part such as a narrow gap with ultraviolet light by allowing an LED chip 10 fixed to a tip portion 22 of an elongated body 20 to emit ultraviolet light described later. Since the LED chip 10 fixed to the tip portion 22 of the elongated body 20 emits ultraviolet light, the light irradiation apparatus 100 is capable of radiating almost all the ultraviolet light emitted by the LED chip 10 to the narrow part and is thus capable of radiating ultraviolet light effectively.

A light irradiation apparatus 100 is provided with an LED chip 10, a cover unit 12, an elongated body 20, and a power supply unit 28. The elongated body 20 is provided with a conductive unit 24 and an insulation unit 26. The power supply unit 28 supplies direct current power that is necessary for the LED chip 10 to emit ultraviolet light via the conductive unit 24.

The LED chip 10 is closely fixed to the tip portion 22 of the elongated body 20 and emits ultraviolet light by electrical power that is supplied from the power supply unit 28 via the conductive unit 24. The LED chip 10 emits ultraviolet light whose center wavelength or peak wavelength is included in a wavelength bandwidth of about 200 nm to 360 nm and has an anode electrode and a cathode electrode that are connected to the conductive unit 24. As such LED chips, those in which aluminum gallium nitride (AlGaN) is used are known. In order to improve disinfection effects, an LED chip capable of radiating ultraviolet light called disinfection rays whose center wavelength is around 260 nm is desirably selected as the LED chip 10. Also, in order for the LED chip 10 to be able to be introduced to a narrow part, the size thereof is desirably around 0.1 mm to 1 mm square.

The cover unit 12 is a member that covers the LED chip 10 and has a role of protecting the LED chip 10 so that, when the elongated body 20 is inserted into a pipe or the like, the LED chip 10 does not directly touch the pipe or the like. Also, the cover unit 12 is a material that allows ultraviolet light emitted by the LED chip 10 to pass therethrough and is desirably a material that hardly receives damages such as chipping and cracking even when the material comes into contact with the pipe or the like. For example, an amorphous fluorine-based resin that has high ultraviolet light transmittance and adequate plasticity may be used as the cover unit 12.

The elongated body 20 is a supporting member for guiding the LED chip 10 fixed to the tip portion 22 to a narrow part such as the inside of a pipe and is a linear-shaped member that is long in one direction having flexibility that allows for elastic restoration. In this case, "having flexibility that allows for elastic restoration" means to have both rigidity that allows the elongated body 20 to pass through the entrance to the inside of the pipe and plasticity that allows for bending without buckling at a bent portion of the pipe.

The conductive unit 24 represents two electrical cables that extend along the longitudinal direction of the elongated body 20 and that pass electric current for allowing the LED chip 10 to emit light, and one end thereof is connected to an anode electrode or a cathode electrode of the LED chip 10 while the other end thereof is connected to the power supply unit 28. The conductive unit 24 desirably has such a degree of plasticity that does not interfere with the plasticity of the elongated body 20, and, for example, a metal wire including a material having high electrical conductivity such as copper or the like may be used.

The insulation unit 26 has a hollow structure that extends in the longitudinal direction of the elongated body 20 and serves as a structure of the elongated body 20 while covering the conductive unit 24 so as to ensure electrical insulation by putting the conductive unit 24 through the area of the hollow. For the insulation unit 26, for example, a resin of polyethylene, nylon, or the like, a fluorine-based resin, or the like may be used as a material that has the rigidity and the plasticity described above. The rigidity may be enhanced, after the conductive unit 24 is put through a hollow area of the insulation unit 26, by filling a gap in the hollow area with a resin according to the rigidity required for the elongated body 20.

With the above configuration, the light irradiation apparatus 100 is capable of effectively irradiating even a narrow part with ultraviolet light. FIG. 2 illustrates the elongated body 20 inserted into a narrow pipe 49 with a small inner diameter d. This figure shows a state where ultraviolet light is radiated to the inside of the pipe 49 from the LED chip 10 attached to the tip portion 22 of the elongated body 20 that is inserted into the pipe 49. For example, when one LED chip of 1 mm square is used as the LED chip 10 and the tip portion 22 is designed to have a circular cylindrical shape of a diameter of 1.5 mm so that the LED chip of 1 mm square can be closely fixed, the diameter of the elongated body 20 is around 1.5 mm. In that case, the elongated body 20 can be inserted into even a narrow pipe with an inner diameter d of around 2 mm, and ultraviolet light can be radiated to the inside thereof. In order to effectively disinfect the inside of the pipe, ultraviolet light is desirably radiated in either of a case where the elongated body 20 is moved in a direction of insertion into the pipe and a case where the elongated body 20 is moved in a direction of withdrawal from the pipe.

If ultraviolet light is guided using an optical fiber, only a portion of ultraviolet light that is emitted by a light source can be guided by the optical fiber in general, and the light intensity thereof becomes attenuated as the ultraviolet light passes through the optical fiber. Thus, the light intensity of the ultraviolet light radiated via the optical fiber represents a part of that of the ultraviolet light emitted by the light source. On the other hand, since the LED chip 10 fixed to the tip portion 22 of the elongated body 20 emits ultraviolet light, the light irradiation apparatus 100 is capable of radiating almost all ultraviolet light emitted by the LED chip 10 to the inside of the pipe 49. Therefore, in the light irradiation apparatus 100, the utilization efficiency of ultraviolet light is high compared to a case where an optical fiber is used, and electrical power that is necessary for radiating ultraviolet light of the same light intensity can be reduced so that electric power consumption is reduced.

FIG. 3 illustrates the elongated body 20 inserted into a bent pipe 50. This figure shows a state where the elongated body 20 is inserted inside the pipe 50 from an entrance 52 of the pipe 50 and the tip portion 22 has reached beyond a bent portion 54 that is bent at a right angle. In order to allow the elongated body 20 to pass through the bent portion 54 that is bent at a right angle, the elongated body 20 needs to be bent such that, with respect to the inner diameter d of the pipe, the curvature radius r of the elongated body 20 passing through the bent portion 54 satisfies the following at this time: $r < 3.4*d$.

If an optical fiber is inserted inside the pipe 50 and ultraviolet light guided by the optical fiber is radiated to the inside of the pipe 50, the optical fiber needs to be used in a range where the curvature radius thereof does not fall below an allowable curvature radius, which is determined in proportion to a core diameter. This is because, if the optical fiber is used while being bent to have a curvature radius that is smaller than a curvature radius that is allowable, light may leak to the outside at a section where the optical fiber is bent, and the fiber may become damaged lowering the light transmission efficiency, thus causing the light intensity of light that is guided to be lowered.

For example, if an optical fiber made of quartz having high ultraviolet light transmittance is used, a curvature radius that is allowable is around twenty times more than the core diameter in general, and, if a quartz fiber having a relatively large core diameter of 500 µm is used in order to increase the light intensity of ultraviolet light that can be guided, a curvature radius that is allowable is 100 mm. In that case, if a quartz fiber having a core diameter of 500 µm is to be put through the pipe 50 having the bent portion 54 that bent at a right angle, the inner diameter d of the pipe that corresponds to an allowable curvature radius r of 100 mm is around 30 mm, and the guiding of light into a pipe having an inner diameter d that is smaller than this becomes difficult. Also, a reduction in the core diameter of the optical fiber allows the optical fiber to cope with a pipe having a small inner diameter. However, the light intensity of light that can be guided by the optical fiber becomes smaller as the core diameter becomes smaller.

Meanwhile, since a material having plasticity that is higher than that of quartz can be used as the elongated body 20 in the light irradiation apparatus 100, a curvature radius that is allowable can be made smaller compared to a quartz fiber having the same diameter. Thus, the elongated body 20 can be inserted into a pipe having a smaller inner diameter so as to radiate ultraviolet light. In particular, even when the elongated body 20 is bent at a curvature radius that is smaller than the allowable curvature radius of a quartz fiber having the same diameter, the value of current supplied to the LED chip 10 is almost unchanged, and the light intensity of ultraviolet light emitted by the LED chip 10 thus does not become lowered. Therefore, the light irradiation apparatus 100 is capable of radiating ultraviolet light effectively to the inside of a bent pipe in which the guiding of light is difficult when an optical fiber is used.

For example, when one LED chip 10 of 1 mm square is used and the diameter of the elongated body 20 is set to be around 1.5 mm, the allowable curvature radius r of the elongated body 20 is 15 mm since the allowable curvature radius of an electrical cable having the insulation unit 26 as a resin material is around ten times more than the diameter in general. In that case, even in the case of a pipe having a bent portion, the elongated body 20 can be inserted into a narrow pipe with an inner diameter d of around 5 mm, which corresponds to the allowable curvature radius r of 15 mm, and ultraviolet light can be radiated to the inside thereof.

FIG. 4 is a diagram illustrating a light irradiation apparatus 200 according to an exemplary variation. In addition to the above-described configuration of the light irradiation apparatus 100 according to the embodiment, the light irradiation apparatus 200 is further provided with a bending mechanism 30 provided near the tip portion 22 of the elongated body 20 and a control unit 46 that allows the bending direction of the tip portion 22 to be controlled from an end portion on the side opposite to the tip portion 22 of the elongated body 20. Having the bending mechanism 30 and the control unit 46 facilitates the passage of the tip portion 22 to deep inside by bending the tip portion 22 in a predetermined direction when putting the elongated body 20 inside a pipe that is bent and also allows the radiation direction of ultraviolet light from the LED chip 10 to be changed.

The bending mechanism 30 is provided with a rotation unit 32 and a holding unit 40. The rotation unit 32 is a member that has a shape where the bottom surface of a cylindrical member is connected with a hemisphere having the same diameter. The LED chip 10 is fixed closely to the top surface of the rotation unit 32 to which the hemisphere is not connected, forming the tip portion 22 of the elongated body 20. An insertion hole 34 is provided in the hemisphere of the rotation unit 32 in a direction perpendicular to the longitudinal direction of the elongated body 20, and a rotating shaft 42 described later is inserted therein. A connector 36 is provided on the side surface of the rotation unit 32 and is connected to the control unit 46 via a wire 48.

The holding unit 40 is provided with a rotating shaft 42 inserted into the insertion hole 34 of the rotation unit 32 and a groove 44 that receives the hemisphere of the rotation unit 32. This allows the holding unit 40 to hold the rotation unit 32 rotatably around the rotating shaft 42.

The control unit 46 has a wire 48 for controlling the bending direction of the bending mechanism 30. The wire 48 is provided extendedly in the longitudinal direction inside the elongated body 20, and one end thereof is connected to the connector 36. The control unit 46 controls the bending direction of the rotation unit 32 by pulling the wire 48 connected to the connector 36. The wire 48 may also serve as a conductive unit 24 that supplies electrical power to the LED chip 10 or may be provided separately from the conductive unit 24.

The invention is not limited to the above-mentioned embodiments, and various modifications, such as a design change, may be added thereto on the basis of knowledge of those skilled in the art. It should be understood that any embodiment to which one or more of the modifications are added is also included in the scope of the invention.

A case has been shown where a light irradiation apparatus is used for the purpose of performing disinfection treatment inside a pipe. However, the light irradiation apparatus may be used for other purposes. For example, when cracks are created at a narrow part inside a pipe or the like, an ultraviolet light curable resin may be applied to fill the cracks, and a light irradiation apparatus according to the present embodiment or exemplary variation may be used for the purpose of hardening the resin by irradiating the applied resin with ultraviolet light.

A case has been shown where an LED chip 10 is closely fixed to a vertical surface of a tip portion 22 with respect to the longitudinal direction of an elongated body 20. However, an inclined plane that has a predetermined angle may be formed on the tip portion 22, and the LED chip 10 may be closely fixed to the inclined plane. This allows for effective irradiation with ultraviolet light not only in the forward direction from the tip portion 22 but also the lateral direction and the backward direction in the elongated body 20 inserted into a tube or the like. The LED chip 10 may be attached to the side surface of the elongated body 20. Alternatively, the LED chip 10 may be attached to the tip portion 22, and a plurality of LED chips 10 may be further attached to the side surface of the elongated body 20.

A case has been shown where one LED chip of 1 mm square is used as the LED chip 10 and the diameter of the elongated body 20 is set to be around 1.5 mm. However, a larger LED chip or a plurality of LED chips may be used while being fixed to the tip portion 22 depending on the light intensity of ultraviolet light that is required. For example, by using four LED chips of 1 mm square and setting the diameter of the elongated body 20 to be around 3 mm, the light intensity of ultraviolet light can be increased compared to a case where only one LED chip is used. On the other hand, in order to cope with narrower sections and intricately bent sections, a smaller LED chip may be used, and the diameter of the elongated body 20 may be set to be smaller.

A case has been shown where an LED chip emits ultraviolet light. However, an LED chip that emits visible light or that emits infrared light may be used.

Also, a case has been shown where the elongated body 20 has flexibility. However, a linear rod-shaped member that does not become easily deformed by external force may be used as an elongated body. For example, if it is necessary, in a narrow part provided with a filter or the like, to irradiate the other side of the filter with light, a site behind the filter can be effectively irradiated with light by inserting the elongated body 20 through the mesh of the filter.

As the bending mechanism 30, a structure that is provided with the rotation unit 32 hold rotatably with respect to the holding unit 40 has been shown. However, a mechanism that allows the tip portion 22 to be bent is not limited to this. For example, a mechanism may be employed where the bending direction is changed by disposing a material whose plasticity is higher than that of the elongated body 20 near the tip portion 22 and applying voltage to a piezoelectric device disposed inside the material. In addition, a bending mechanism in which a shape memory alloy is used may be employed.

It should be understood that the invention is not limited to the above-described embodiment, but may be modified into various forms on the basis of the spirit of the invention. Additionally, the modifications are included in the scope of the invention.

What is claimed is:

1. A light irradiation apparatus comprising:
   an elongated body that is linear shaped member that is long in one direction and that has flexibility that allows for elastic restoration;
   a light emitting diode (LED) chip that is closely fixed to a tip portion of the elongated body and that emits ultraviolet light; and
   a cover unit that is formed of a material that covers the LED chip so as to protect the LED chip and allows the ultraviolet light emitted by the LED chip to pass therethrough,
   wherein the elongated body has:
   a conductive unit that extends in a longitudinal direction of the elongated body and that passes electric current for allowing the LED chip to emit light; and
   an insulation unit that covers the conductive unit so as to ensure electrical insulation of the conductive unit, and
   wherein the light irradiation apparatus is used for disinfection treatment of an object by allowing the LED chip to emit light while the elongated body is inserted into a narrow part.

2. The light irradiation apparatus according to claim 1, wherein the LED chip has a size of 0.1 mm to 1 mm square.

3. The light irradiation apparatus according to claim 1, wherein the cover unit is formed of a resin.

4. The light irradiation apparatus according to claim 3, wherein the cover unit is formed of an amorphous fluorine-based resin.

5. The light irradiation apparatus according to claim 1, wherein the light irradiation apparatus is used for disinfection treatment of the inside of a pipe by allowing the LED chip to emit light while the elongated body is inserted in the pipe.

6. The light irradiation apparatus according to claim 5, wherein the elongated body is inserted into the inside of the pipe having a bent portion when using the light irradiation apparatus.

7. The light irradiation apparatus according to claim 5, wherein the elongated body have both rigidity that allows the elongated body to pass through the entrance to the inside of the pipe and plasticity that allows the elongated body to bend without buckling at a bent portion of the pipe.

8. The light irradiation apparatus according to claim 5, wherein the elongated body is moved in a direction of insertion into the pipe and in a direction withdrawal from the pipe when using the light irradiation apparatus.

9. The light irradiation apparatus according to claim 5, wherein the LED chip emits the ultraviolet light in at least either of a case where the elongated body is moved in a direction of insertion into the pipe and a case where the elongated body is moved in a direction of withdrawal from the pipe.

10. The light irradiation apparatus according to claim 5, wherein the LED chip is closely fixed to a vertical surface of the tip portion of the elongated body, the vertical surface being perpendicular to the longitudinal direction of the elongated body.

11. The light irradiation apparatus according to claim 1, further comprising:
    a bending mechanism that is provided near the tip portion and that allows a vicinity of the tip portion to be bent; and
    a control unit that allows a bending direction by the bending mechanism to be controlled from an end portion on the side opposite to the tip portion in the elongated body.

12. The light irradiation apparatus according to claim 1, wherein the LED chip emits the ultraviolet light of which center wavelength of peak wavelength is included in a wavelength bandwidth of 200 nm to 360 nm.

* * * * *